US00PP09913P

United States Patent [19]

Zeliff

[11] Patent Number: Plant 9,913

[45] Date of Patent: Jun. 3, 1997

[54] CHRYSANTHEMUM PLANT NAMED 'COPPER CHARM'

[75] Inventor: Robert W. Zeliff, Palmetto, Fla.

[73] Assignee: Manatee Fruit Company, Palmetto, Fla.

[21] Appl. No.: 632,133

[22] Filed: Apr. 15, 1996

[51] Int. Cl.[6] ..... A01H 5/00

[52] U.S. Cl. ..... Plt./79

[58] Field of Search ..... Plt./76, 79

*Primary Examiner*—Howard J. Locker

*Attorney, Agent, or Firm*—Foley & Lardner

[57] ABSTRACT

A Chrysanthemum plant named Copper Charm particularly characterized by its flat capitulum form; decorative capitulum type; copper-bronze ray floret color; diameter across face of capitulum of 101 to 121 mm when fully opened, when grown as a pinched disbudded pot mum; photoperiodic flowering response to short days of 53 to 59 days; plant height, with 14 to 16 long days after sticking unrooted cuttings and with 1 to 2 applications of 2500 ppm B-9 SP, ranges from 23 to 28 cm when grown as a pinched pot mum with 4 cuttings in a 15 cm pot; branching pattern is spreading, each plant developing 4 to 6 laterals after pinch; and recommended as a disbudded pot mum.

1 Drawing Sheet

The present invention comprises a new and distinct cultivar of Chrysanthemum, botanically known as *Dendranthema grandiflora,* and referred to by the cultivar name Copper Charm.

Copper Charm, identified as 6954 (92-#02149) is a spontaneous mutation of the cultivar Dark Bronze Charm, disclosed in U.S. Plant Pat. No. 6,801, and was selected to expand the color range of the parental variety.

Copper Charm was discovered and selected by inventor Robert W. Zeliff as one flowering plant within a flowering block of Dark Bronze Charm in August of 1992 in a controlled environment in Cortez, Fla.

The first act of asexual reproduction of Copper Charm was accomplished when vegetative cuttings were taken from the initial selection in November of 1992 in a controlled environment in Cortez, Fla., by Robert W. Zeliff.

Horticultural examination of controlled flowerings of successive plantings has shown that the unique combination of characteristics as herein disclosed for Copper Charm are firmly fixed and are retained through successive generations of asexual reproduction.

Copper Charm has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Copper Charm, which, in combination, distinguish this Chrysanthemum as a new and distinct cultivar:

1. Flat capitulum form.
2. Decorative capitulum type.
3. Copper-bronze ray floret color.
4. Diameter across face of capitulum of 101 to 121 mm when fully opened, when grown as a pinched disbudded pot mum.
5. Photoperiodic flowering response to short days of 53 to 59 days.
6. Plant height, with 14 to 16 long days after sticking unrooted cuttings and with 1 to 2 applications of 2500 ppm B-9 SP, ranges from 23 to 28 cm when grown as a pinched pot mum with 4 cuttings in a 15 cm pot.

7. Branching pattern is spreading, each plant developing 4 to 6 laterals after pinch.
8. Recommended as a disbudded pot mum.

The accompanying photographic drawing is a side view of a potted mum of Copper Charm, with 4 cuttings in a 15 cm pot, with the colors being as nearly true as possible with illustrations of this type.

Of the commercial cultivars known to the inventor, the most similar in comparison to Copper Charm is the parent cultivar Dark Bronze Charm. All traits of Copper Charm are similar to those of Dark Bronze Charm, except for the ray floret color. The ray floret color of Copper Charm is significantly darker (RHS 169B to 171B) than the ray floret color of Dark Bronze Charm (RHS 167B to 168C).

In the following description color references are made to The Royal Horticultural Society Colour Chart. The color values were determined on plant material grown as a pinched disbudded pot mum in Salinas, Calif. on May 22, 1995.

Classification:

*Botanical.*—*Dendranthema grandiflora* cv Copper Charm.

*Commerical.*—Flat decorative disbud pot mum.

INFLORESCENCE

A. Capitulum:

*Form.*—Flat.

*Type.*—Decorative.

*Diameter across face.*—101 to 121 mm when fully opened.

B. Corolla of ray florets:

*Color (general tonality from a distance of three meters)* .—Copper-bronze.

*Color (upper surface).*—169B to 171B.

*Color (under surface).*—173C to 173D.

*Shape.*—Flat, straight.

C. Corolla of disc florets:

*Color (mature).*—154B to 154C.

*Color (immature).*—164B.

D. Reproductive organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum with 14 to 16 long days after sticking unrooted cuttings prior to start of short days, with 1 to 2 applications of 2500 ppm B-9 SP.

*Branching pattern.*—Spreading, each plant developing 4 to 6 laterals after pinch.

B. Foliage:

*Color* (*upper surface*).—147A.

*Color under surface*).—147B.

*Shape.*—Lobed and serrated.

What is claimed is:

1. A new and distinct Chrysanthemum plant named Copper Charm, as described and illustrated.

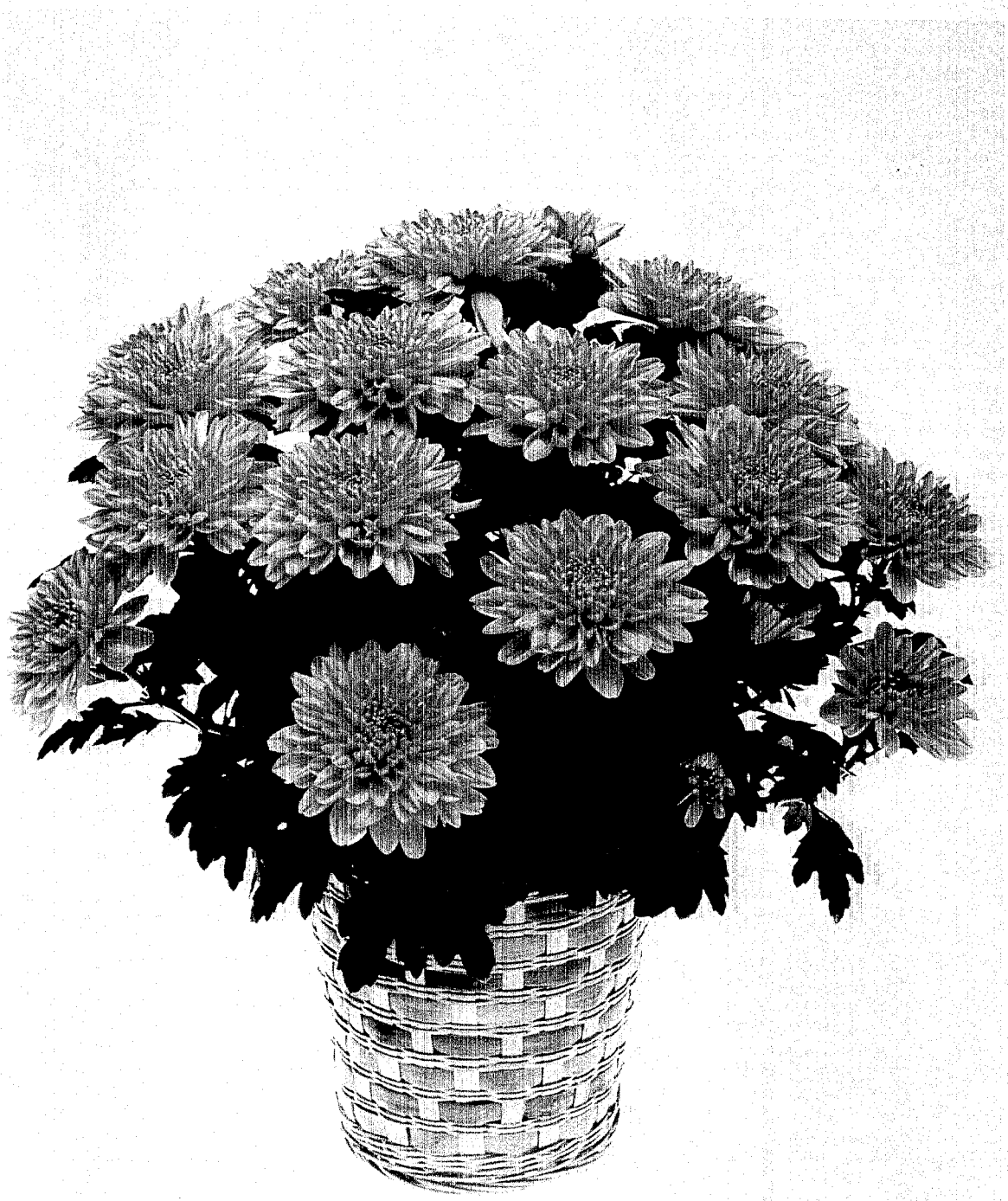

* * * * *